United States Patent [19]

Konotsune et al.

[11] 4,070,536
[45] Jan. 24, 1978

[54] PROCESS FOR THE PREPARATION OF 4-BENZOYLPYRAZOLE DERIVATIVES

[75] Inventors: Takuo Konotsune; Takashi Matsui; Junzo Tobitsuka, all of Tokyo, Japan

[73] Assignee: Sankyo Company Limited, Tokyo, Japan

[21] Appl. No.: 691,476

[22] Filed: June 1, 1976

[30] Foreign Application Priority Data

June 19, 1975 Japan ................................. 50-74962
June 19, 1975 Japan ................................. 50-74963

[51] Int. Cl.$^2$ .......................................... C07D 231/20
[52] U.S. Cl. .................................................. 548/367
[58] Field of Search .............................. 260/310 A

[56] References Cited

PUBLICATIONS

Jensen, Acta. Chem. Scan., vol. 13, (1959) pp. 1668–1670.
Noller, Chemistry of Organic Compounds, (1965) published by W. B. Saunders Co., Phila. Pa., pp. 585 & 586.
The Merck Index, 8th Ed. (1968) published by Merck & Co. Rahway, N. Y., p. 1168.

*Primary Examiner*—Donald B. Moyer
*Attorney, Agent, or Firm*—Toren, McGeady and Stanger

[57] ABSTRACT

4-Benzoyl-5-hydroxypyrazole derivatives are prepared by treating 5-benzoyloxypyrazole derivatives with more than 1 equivalent mole of alkaline substance or more than 1 mole of aluminum chloride per mole of the 5-benzoyloxypyrazole derivatives. The desired pyrazole derivatives are useful as a herbicide.

5 Claims, No Drawings

PROCESS FOR THE PREPARATION OF 4-BENZOYLPYRAZOLE DERIVATIVES

This invention relates to a novel process for the preparation of 4-benzoylpyrazole derivatives useful as a herbicide.

More particularly, it relates to a process for the preparation of 4-benzoylpyrazole derivative having the formula

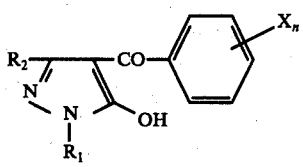

(I)

wherein $R_1$ represents an alkyl group having from one to 3 carbon atoms or an alkenyl group having 3 or 4 carbon atoms, $R_2$ represents an alkyl group having from one to 3 carbon atoms, X represents a halogen atom, an alkyl group having from one to 4 carbon atoms, an alkoxy group having from one to 4 carbon atoms or nitro group and $n$ is an integer from 1 to 3, provided that when $n$ is an integer of 2 or 3, X may be the same or different each other and a metal salt thereof.

The compound of the above formula (I) may exist as its tautomer forms as shown below,

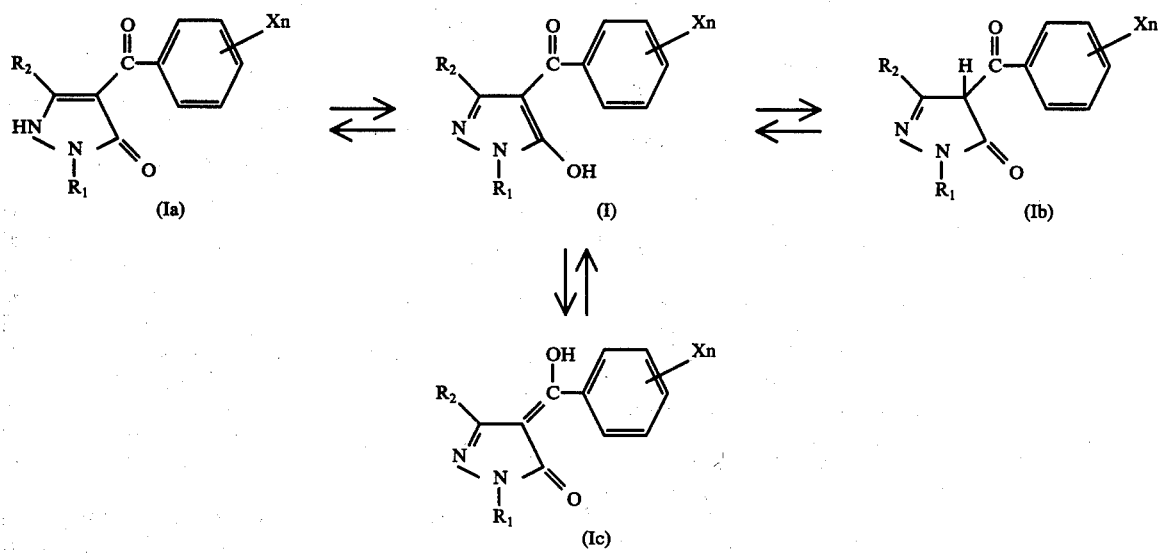

In the above general formula (I), $R_1$ is preferably an alkyl group of a straight or branched chain containing 1-3 carbon atoms such as methyl, ethyl, n-propyl or isopropyl, and most preferably methyl group; or an alkenyl group of a straight or branched chain containing 3 or 4 carbon atoms such as 1-methyl-2-propenyl, 2-methyl-2-propenyl, allyl, 2-butenyl or 3-butenyl group, and most preferably allyl group.

$R_2$ is preferably an alkyl group of a straight or branched chain containing 1-3 carbon atoms such as methyl, ethyl, n-propyl or isopropyl, and most preferably methyl group. X represents preferably a halogen atom such as chlorine, bromine, fluorine or iodine, and most preferably chlorine atom; nitro group; an alkyl group of a straight or branched chain containing 1-4 carbon atoms such as methyl, ethyl, n-propyl, isopropyl, n-butyl, isobutyl or tert-butyl, and most preferably methyl group; or an alkoxy group of a straight or branched chain containing 1-4 carbon atoms such as methoxy, ethoxy, n-propoxy, isopropoxy, n-butoxy or isobutoxy, and most preferably methoxy group. The most preferable compounds are those having the formula

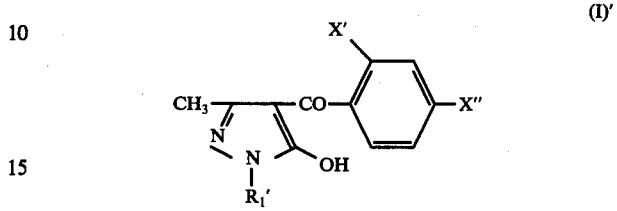

(I)' wherein $R_1'$ is methyl or allyl, X' and X" are the same or different and each is chlorine or nitro.

As metal salts of the compounds (I) are involved, for example, those with an ion of an alkali metal such as lithium, sodium or potassium, or of an alkaline earth metal such as calcium or magnesium.

Previously, we have been found that the 4-benzoylpyrazole derivatives (I) exhibit a potent herbicidal activity and filed a patent application as Ser. No. 558,682 in U.S.A.

Theretofore, it has been reported that 1,3-dimethyl-4-(2-chlorobenzoyl)-5-hydroxypyrazole and 1,3-dimethyl-4-(4-nitrobenzoyl)-5-hydroxypyrazole may be prepared by reacting 1,3-dimethylpyrazolone with corresponding substituted bonzoyl chlorides at an elevated temperature in a suspension of calcium oxide or triethylamine in dioxane, pyridine, dimethylformamide or benzene. However, the yield of the product is about 70–75% even under the best reaction conditions using a suspension of calcium oxide in dioxane, and moreover a 0-benzoyl derivative is also formed as a by-product (Chimiya Geterotsiklicheskith Soedinenii, 799, 1972).

And further, by the method described in the above cited literature, benzoylation at the 4-position of pyrazolone with 2,4-dichlorobenzoic acid does not proceed with ease affording the compound of the above formula (I) in below 50% yield with liberation of a large amount of 2,4-dichlorobenzoic acid.

As a result of extensive investigations on the industrially useful process for preparing 4-benzoylpyrazole derivatives, the present invention has been completed by discovering the following procedure: The rearrangement reaction of benzoyl group in the pyrazole ring into the 4-position is carried out by utilizing an alkaline substance or aluminum chloride as a catalyst affording the 4-benzoylpyrazole derivatives and metal salt thereof in good yield with less formation of by-products as compared with the method of direct benzoylation at the 4-position of the pyrazolone ring.

According to the present invention, the 4-benzoylpyrazole derivatives (I) can be prepared by treating a pyrazole derivatives having the formula

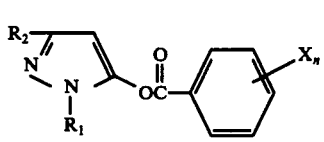

(II)

wherein $R_1$, $R_2$, X and $n$ have the same meanings as defined above with more than 1 equivalent mole of alkaline substance or more than 1 mole of aluminum chloride per mole of the pyrazole derivatives (II).

In practising the process of this invention, the reaction is smoothly carried out by contacting the compounds (II) with more than 1 equivalent mole of an alkaline substance or more than 1 mole of aluminum chloride per mole of the compound (II) under stirring. Representative examples of the alkaline substance include an alkali- or alkaline earth metal carbonate, e.g., sodium carbonate, potassium carbonate; an alkali or alkaline earth metal hydroxide, e.g., sodium hydroxide, calcium hydroxide, magnesium hydroxide; an alkali or alkaline earth metal cyanide, e.g., calcium cyanide; and an alkali or alkaline earth metal alkoxide, e.g., sodium methoxide, potassium ethoxide, sodium isopropoxide, potassium tert-butoxide.

The alkaline substance should be used in an amount of more than 1 equivalent mole, preferably 1.1–6.0 equivalent moles and most preferably 1.5–3.0 equivalent moles, per mole of the pyrazole derivative (II).

The alkaline substance is preferably pulverized as fine as possible and mixed with the compound (II). The mixture is fused and agitated under heating. Alternatively it is reacted under heating and stirring in the presence of a solvent at 80°–200° C. preferably at 100°–160° C. The reaction time required is usually from 30 minutes to 5 hours. The solvent may be employed without any particular limitation, so far as it does not participate in the reaction. As examples of such solvents are mentioned a lower alcohol such as isopropanol, tert-butanol and the like; an ether such as dioxane, diisopropyl ether, tetrahydrofuran and the like, and a mixture thereof such as tetrahydrofuran-dioxane and the like; or a ketone such as methyl ethyl ketone, diethyl ketone and the like, and most preferably a lower alcohol and an ether are employed.

The reaction mixture in the absence of a solvent often solidifies gradually as the rearrangement reaction proceeds, becoming difficult to be agitated. In such a case, an appropriate amount of the aforementioned solvent may be added. THe important thing is to keep good contact of the catalyst with the compound of the formula (II), but the amount of a solvent to be used is desirable to be small as far as possible. Although the presence of a small amount of water is preferable to acceralate the reaction to proceed, but it accompanies at the same time the increased formation of free benzoic acid, and therefore the water content in the solvent is desirably within 1%.

After the reaction is completed, the end product of the present invention can be recovered from the reaction mixture by a conventional method. For instance, after the completion of reaction, the solvent is removed from the reaction mixture leaving the desired compound as a salt of an alkali metal or alkaline earth metal which is employed as a catalyst for the rearrangement reaction. The end product can be usually isolated in a free state by adjusting the pH at less than 3 by the addition of an acid to the salt obtained as above.

In case where the aluminum chloride is used, it should be used in an amount of more than 1 mole, preferably 1.1–2.0 moles per mole of the pyrazole derivative (II). The upper limit of the amount should be about 3 moles in view of the convenient operation of the reaction and the economical standpoint.

The reaction may be carried out in the presence or absence of a solvent, but it is preferable to employ a solvent in order to make the reaction to proceed smoothly. The solvent may be employed without any particular limitation, so far as it does not participate in the reaction. As examples of such solvents are mentioned a halogenated aliphatic hydrocarbon such as dichloroethane, tetrachloroethane, chloroform and the like, a halogenated aromatic hydrocarbon such as monochlorobenzene and the like, a halogenated aliphatic hydrocarbon being preferably utilized. The reaction temperature is not critical, but it is usually carried out in the range from the room temperature to 150° C. The reaction time is usually between 10 minutes to 5 hours.

After the reaction is completed, the product may be recovered from the reaction mixture by a conventional manner. For instance, water is added to the reaction mixture, the organic layer separated after stirring, the solvent removed from the solution to give the desired product as an aluminum salt. The aluminum salt thus prepared can be converted into the compound of the formula (I) in a free state by stirring and mixing in a strong acid (below pH 1). Further purification may be performed by a usual technique such as recrystallization and others.

Among the compounds of the above formula (I) which may be prepared by the process of the invention and metal salts thereof, the following are mentioned as representatives:
1. 1-Ethyl-3-methyl-4-(2,4-dichlorobenzoyl)-5-hydroxypyrazole; m.p. 176°–177° C
2. 1,3-Dimethyl-4-(2-chlorobenzoyl)-5-hydroxypyrazole; m.p. 154°–155° C
3. 1,3-Dimethyl-4-(2,4-dichlorobenzoyl)-5-hydroxypyrazole; m.p. 165°–166° C
4. 1,3-Dimethyl-4-(2-bromobenzoyl)-5-hydroxypyrazole; m.p. 154°–156° C
5. 1,3-Dimethyl-4-(3,4-dimethoxybenzoyl)-5-hydroxypyrazole; m.p. 154°–155° C
6. 1,3-Dimethyl-4-(2-chloro-4-nitrobenzoyl)-5-hydroxypyrazole; m.p. 197°–197.5° C
7. 1,3-Dimethyl-4-(3,4,5-trimethoxybenzoyl)-5-hydroxypyrazole; m.p. 189°–191° C 8. 1,3-Dimethyl-4-(2-nitro-4-chlorobenzoyl)-5-hydroxypyrazole; m.p. 223°-224° C
9. 1-Allyl-3-methyl-4-(2,4-dichlorobenzoyl)-5-hydroxypyrazole; m.p. 161°-163° C
10. 1,3-Dimethyl-4-(2-iodobenzoyl)-5-hydroxypyrazole; m.p. 171°-172° C
11. 1,3-Dimethyl-4-(4-methylbenzoyl)-5-hydroxypyrazole; m.p. 114°-116° C
12. 1,3-Dimethyl-4-(2-methoxybenzoyl)-5-hydroxypyrazole; m.p. 162.5°-163.5° C
13. 1,3-Dimethyl-4-(4-nitrobenzoyl)-5-hydroxypyrazole; m.p. 234°-235° C
14. 1,3-Dimethyl-4-(2,4-dichlorobenzoyl)-5-hydroxypyrazole Calcium Salt; m.p. ca. 260° C
15. 1,3-Dimethyl-4-(2-nitrobenzoyl)-5-hydroxypyrazole; m.p. 233°-234° C
16. 1,3-Dimethyl-4-(2,5-dichlorobenzoyl)-5-hydroxypyrazole; m.p. 183°-184° C
17. 1,3-Dimethyl-4-(2,4-dichlorobenzoyl)-5-hydroxypyrazole Magnesium Salt; m.p. ca. 270° C
18. 1-Ethyl-3-methyl-4-(2-nitro-4-chlorobenzoyl)-5-hydroxypyrazole; m.p. 196°-197° C
19. 1,3-Dimethyl-4-(2,4-dichlorobenzoyl)-5-hydroxypyrazole Copper Salt; m.p. over 300° C
20. 1,3-Dimethyl-4-(2,4-dichlorobenzoyl)-5-hydroxypyrazole Sodium Salt; m.p. over 300° C
21. 1-Methyl-3-n-propyl-4-(2-chlorobenzoyl)-5-hydroxypyrazole; m.p. 125°-126° C
22. 1,3-Dimethyl-4-(2,4,5-trichlorobenzoyl)-5-hydroxypyrazole; m.p. 156°-157° C
23. 1,3-Dimethyl-4-(2-methylbenzoyl)-5-hydroxypyrazole; m.p. 82°-83° C
24. 1,3-Dimethyl-4-(2-fluorobenzoyl)-5-hydroxypyrazole; m.p. 158°-159° C
25. 1,3-Dimethyl-4-(4-tert-butylbenzoyl)-5-hydroxypyrazole; m.p. 172°-173° C
26. 1,3-Dimethyl-4-(3,4-dimethylbenzoyl)-5-hydroxypyrazole; m.p. 197°-198° C
27. 1,3-Dimethyl-4-(3,5-dimethylbenzoyl)-5-hydroxypyrazole; m.p. 165°-167° C
28. 1,3-Dimethyl-4-(2,4-dimethylbenzoyl)-5-hydroxypyrazole; m.p. 95°-96° C The pyrazole derivatives (II) employed as starting materials in this invention are novel and can be preferably prepared by pyrazolone derivatives having the formula

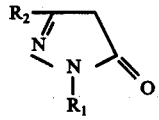

(III)

wherein $R_1$ and $R_2$ have the same meanings as defined above with benzoic acid derivatives (IV)

wherein X and n have the same meanings as defined above or anhydrides or halides, preferably the chlorides, thereof.

The reaction may be carried out by contacting the compound (III) with the compound (IV) in the presence of an acid binding agent and an inert solvent. Examples of the acid binding agent include an alkali metal carbonate, e.g., sodium carbonate, potassium carbonate; an alkaline earth metal hydroxide, e.g., calcium hydroxide; a tertiary amine, e.g., pyridine, triethylamine, dimethylaniline. As the solvent, there may be used aprotic solvents such as aromatic hydrocarbons, e.g., benzene, xylene; halogenated aromatic hydrocarbons, e.g., chloroform, dichloroethane, tetrachloroethane; and ethers, e.g., diethyl ether, tetrahydrofuran, dioxane; preferably, benzene, xylene and dichloroethane. It is desirable to use a mixture of said solvent and water in order to separate a salt formed in the reaction system.

Alternatively, the reaction may be carried out by heating a mixture of the compound (III) and the compound (IV) in the absence of a solvent.

Following examples are given for the purpose of the illustration of this invention.

EXAMPLE 1

1,3-Dimethyl-4-(2,4-dichlorobenzoyl)-5-hydroxypyrazole

1. A mixture of 2.85g of 1,3-dimethyl-5-(2,4-dichlorobenzoyloxy)pyrazole and 2.5g of anhydrous sodium carbonate is heated. After the crystals have melted at about 100° C, stirring is continued at 120°-150° C until the mixture soliddifies, about 30-60 minutes being required. Subsequently 10ml of isopropanol is added to the mixture and stirred for further 60 minutes under heating. On cooling the mixture, sodium salt of 1,3-dimethyl-4-(2,4-dichlorobenzoyl)-5-hydroxypyrazole crystallizes out. To the reaction mixture are added 10ml of 6N-hydrochloric acid and 30ml of benzene and the mixture stirred. After the solid substance is dissolved, the benzene layer is separated and condensed to deposit crystals which are washed with methanol affording 2.28g of the desired product of m.p. 165°-166° C as pale yellow crystals. Yield, 80%.

Elementary analysis for $C_{12}H_{10}Cl_2N_2O_2$: Calculated: C, 50.55; H, 3.54; N, 9.82; Cl, 24.87. Found: C, 50.70; H, 3.52; N, 9.86; Cl, 24.77.

2. The procedure of Example (1) is repeated using 1.0g of sodium methoxide instead of 2.5g of sodium carbonate and isopropanol to give the desired product in 71% yield.

3. The procedure of Example (1) is repeated using 3.0g of potassium carbonate instead of 2.5g of sodium carbonate to give the desired product in 80% yield. The infrared spectra of the compounds obtained in Example (1), (2), and (3) are completely superimposable.

4. A mixture of 28.5g of 1,3-dimethyl-5-(2,4-dichlorobenzoyloxy)pyrazole and 20.0g of aluminum chloride in 100ml of dichloroethane is stirred at room temperature for 60 minutes, 25ml of conc. hydrochloric acid (35%) and 50ml of water are then added and stirring is continued for further 60 minutes under heating. After the reaction mixture is cooled, the water layer is removed from the mixture, and the solvent evaporated from the organic layer affording 22.8g of crude desired compound. Yield, 80%. m.p. 165°-166° C after recrystallization from methanol.

Elementary analysis for $C_{12}H_{10}Cl_2N_2O_2$: Calculated: C, 50.55; H, 3.54; N, 9.82; Cl, 24.87. Found: C, 50.21; H, 3.48; N, 9.71; Cl, 24.54.

The benzoylation reaction of 1,3-dimethylpyrazolone with 2,4-dichlorobenzoyl chloride in the presence of 1.0g of calcium hydroxide was performed according to the known method (Acta Chemica Scandinavica, 13, 1668) and the yield of benzoylated product at the 4-position of pyrazolone ring was below 50% and a large amount of 2,4-dichlorobenzoic acid was formed as a by-product.

EXAMPLE 2

1,3-Dimethyl-4-(4-methylbenzoyl)-5-hydroxyprazole

Using 2.3g of 1,3-dimethyl-5-(4-methylenzoyloxy)-pyrazole, 2.5g of anhydrous sodium carbonate and 5ml of isopropanol, the reaction and treatment after completion of the reaction are performed by the same way as in (1) in Example 1 affording 1.2g of the desired product of m.p. 114°–116° C as pale yellow prisms. Yield, 52%.

Elementary analysis for $C_{13}H_{14}N_2O_2$: Calculated: C, 67.81; H, 6.28; N, 12.17. Found: C, 67.50; H, 6.13; N, 12.21.

EXAMPLE 3

1,3-Dimethyl-4-(3,4,5-trimethoxybenzoyl)-5-hydroxypyrazole

Using 3.06g of 1,3-dimethyl-5-(3,4,5-trimethoxybenzoyloxy)pyrazole and 0.75g of calcium hydroxide, the reaction and treatment after completion of the reaction are performed by the same way as in (1) in Example 1 affording 1.7g of the product of m.p. 189°–191° C as colorless prisms. Yield, 55%.

Elementary analysis for $C_{15}H_{18}N_2O_5$: Calculated: C, 58.82; H, 5.92; N, 9.15. Found: C, 58.69; H, 5.88; N, 9.26.

EXAMPLE 4

1,3-Dimethyl-4-(2-nitro-4-chlorobenzoyl)-5-hydroxypyrazole

Using 2.96g of 1,3-dimethyl-5-(2-nitro-4-chlorobenzoyloxy)pyrazole and 0.75g of calcium hydroxide, the reaction and treatment after completion of the reaction are performed by the same way as in (1) in Example 1 affording 1.57g of the product of m.p. 223°–224° C as pale yellow crystals. Yield, 53%.

Elementary analysis for $C_{12}H_{10}N_3O_4Cl$: Calculated: C, 48.75; H, 3.41; N, 14.21; Cl, 11.99. Found: C, 48.89; H, 3.52; N, 14.27; Cl, 11.92.

EXAMPLE 5

1,3-Dimethyl-4-(4-chlorobenzoyl)-5-hydroxypyrazole Aluminum Salt

To 25.1g of 1,3-dimethyl-5-(4-chlorobenzoyloxy)-pyrazole is added 15.0g of aluminum chloride and the mixture stirred for 60 minutes under heating at about 120° C. After the reaction is completed, 100ml of benzene is gradually added to cool the reaction mixture and then 100ml of water added. The mixture is stirred and the organic layer separated, the solvent removed from the solution under reduced pressur to give 23.6g of the desired compound. Yield, 91%. m.p. 282°–284° C after recrystallization from benzene-n-hexane.

Elementary analysis for $C_{12}H_{10}N_2O_2Cl$ Al/3: Calculated: C, 55.72; H, 3.90; N, 10.83; Cl, 13.71. Found: C, 55.24; H, 3.87; N, 10.58; Cl, 14.05.

EXAMPLE 6

1,3-Dimethyl-4-(2-chlorobenzoyl)-5-hydroxypyrazole Aluminum Salt

Using 25.1g of 1,3-dimethyl-5-(2-chlorobenzoyloxy)-pyrazole instead of 25.1g of 1,3-dimethyl-5-(4-chlorobenzoyloxy)pyrazole in Example 5, the same reaction is carried out and treated after completion of the reaction affording 21.7g of the desired compound of m.p. 295°–301° C. Yield, 84% .

Elementary analysis for $C_{12}H_{10}N_2O_2Cl$ Al/3: Calculated: C, 55.72; H, 3.90; N, 10.83; Cl, 13.71. Found: C, 55.44; H, 3.93; N, 10.42; Cl, 13.71.

EXAMPLE 7

1,3-Dimethyl-4-(2,4-dichlorobenzoyl)-5-hydroxypyrazole Aluminum Salt

To 28.5g of 1,3-dimethyl-5-(2,4-dichlorobenzoyloxy)-pyrazole is added 15.0g of aluminum chloride and the mixture is fused and stirred for 60 minutes under heating at 120° C. After completion of the reaction, 100ml of dichloroethane is dropwise added to the reaction mixture under cooling and then 80ml of water added. After stirring the mixture, the organic layer is separated and the solvent removed from the solution to give 24g of the desired compound of m.p. ca. 155° C. Yield, 82%.

Elementary analysis for $C_{12}H_9N_2O_2Cl_2$ Al/3: Calculated: C, 49.17; H, 3.09; N, 9.55; Cl, 24.19; Found: C, 49.22; H, 3.30; N, 9.18; Cl, 23.13.

EXAMPLE 8

1,3-Dimethyl-4-(2-methylbenzoyl)-5-hydroxypyrazole

A mixture of 2.3g of 1,3-dimethyl-5-(2-methylbenzoyloxy)pyrazole and 2.0g of aluminum chloride in 10ml of dichloroethane is stirred for about 60 minutes under heating. After the reaction mixture is cooled, 10ml of water, 2.5ml of conc. hydrochloric acid (35%) and 20ml of dichloroethane are added, and the mixture is refluxed for about 60 minutes under heating. The organic layer is separated from the cooled reaction mixture, the solvent removed under reduced pressure affording 2.2g of a redbrown oily residue, which is crystallized from a small amount of methanol to give the desired compound of m.p. 82°–83° C as pale brown crystals.

Elementary analysis for $C_{13}H_{14}N_2O_2$: Calculated: C, 67.81; H, 6.28; N, 12.17; Found: C, 67.70; H, 6.03; N, 12.26.

PREPARATION OF THE STARTING MATERIALS 1. 1,3-Dimethyl-5-(2,4-dichlorobenzoyloxy)-pyrazole To a mixture of 150ml of benzene and 20ml of water are added 11.2g of 1,3-dimethylpyrazolone, 20.9g of 2,4-dichlorobenzoyl chloride and 5.3g of anhydrous sodium carbonate. The mixture is stirred for 60 minutes and the aqueous layer is removed. The benzene layer is subjected to distillation under reduced pressure to give 25.6g of 1,3-dimethyl-5-(2,4-dichlorobenzoyloxy)-pyrazole. Yield, 90%. The product is recristallized from benzene-n-hexane to afford white needle melting at 99°–100° C.

Elementary analysis for $C_{12}H_{10}Cl_2N_2O_2$: Calculated: C, 50.55; H, 3.54; N, 9.82; Cl, 24.87. Found: C, 50.70; H, 3.52; N, 9.80; Cl, 24.77.

Following the same procedure of the above preparation (1), there are obtained:

1,3-Dimethyl-5-(2-nitro-4-chlorobenzoyloxy)pyrazole; m.p. 119°-121° C 1,3-Dimethyl-5-(2-chlorobenzoyloxy)pyrazole; m.p. 43°-45° C 1,3-Dimethyl-5-(2-methylbenzoyloxy)pyrazole; m.p. 40°-42° C 1,3-Dimethyl-5-(3-chlorobenzoyloxy)pyrazole; m.p. 38°-40.5° C 1,3-Dimethyl-5-(2,5-dichlorobenzoyloxy)pyrazole; m.p. 144° C 1,3-Dimethyl-5-(2,5-dinitrobenzoyloxy)pyrazole; m.p. 181°-182° C 1,3-Dimethyl-5-(2-nitro-5-methylbenzoyloxy)pyrazole; m.p. 124°-125° C 1,3-Dimethyl-5-(2-iodobenzoyloxy)pyrazole; m.p. 78°-79° C 1,3-Dimethyl-5-(4,6-dimethylbenzoyloxy)pyrazole; m.p. 80°-81° C 1,3-Dimethyl-5-(4-nitrobenzoyloxy)pyrazole; m.p. 125° C 1,3-Dimethyl-5-(2-methoxybenzoyloxy)pyrazole; m.p. 52°-54° C 1-Allyl-3-methyl-5-(2,4-dichlorobenzoyloxy)pyrazole; m.p. 43°-44° C 2. 1,3-Dimethyl-5-(4-chlorobenzoyloxy)-pyrazole To 200ml of benzene are added 11.2g of 1,3-dimethyl-pyrazolone, 17.5g of 4-chlorobenzoyl chloride and 10.2g of triethylamine. The mixture is stirred for 30 minutes. After washing with 100ml of water, the solvent is distilled off under reduced pressure. The residue is recristallized from n-hexane to give 23.6g of 1,3-dimethyl-5-(4-chlorobenzoyloxy)pyrazole melting at 100°-101° C. Yield, 94%.

Elementary analysis for $C_{12}H_{11}ClN_2O_2$: Calculated: C, 57.50; H, 4.42; N, 11.18; Cl, 14.14. Found: C, 57.65; H, 4.40; N, 11.16; Cl, 14.04.

What is claimed is:

1. In a process for the the preparation of a 4-benzoyl-pyrazole derivative having the formula

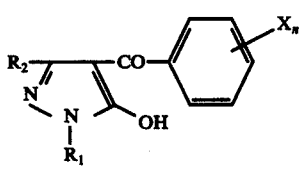

(I)

wherein
$R_1$ represents an alkyl group having from 1 to 3 carbon atoms or an alkenyl group having 3 or 4 carbon atoms,
$R_2$ represents an alkyl group having from 1 to 3 carbon atoms,
X represents a halogen atom, an alkyl group having from 1 to 4 carbon atoms, an alkoxy group having from 1 to 4 carbon atoms or nitro group and
n is an integer from 1 to 3, provided that when n is an integer of 2 or 3, X may be the same or different from each other or a metal salt thereof wherein a pyrazole derivative having the formula

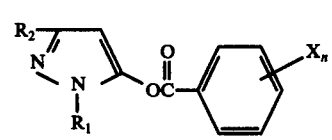

(II)

wherein $R_1$, $R_2$, X and n have the same meaning as defined above is treated with a catalyst, the improvement which comprises said catalyst being an alkali metal carbonate in an amount of more than 1 equivalent mole per mole of the pyrazole derivative (II).

2. A process as claimed in claim 1 in which the alkali metal carbonate is used in an amount of 1.5-3.0 equivalent moles per mole of the pyrazole derivative (II).

3. A process as claimed in claim 1 in which the alkali metal carbonate is sodium or potassium carbonate.

4. In a process for the preparation of a 4-benzoyl-pyrazole derivative having the formula

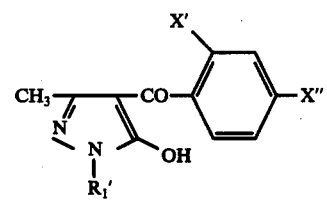

(I)' wherein
$R_1'$ is methyl or alkyl,
X' and X'' are the same or different and each is chlorine or nitro or a metal salt thereof wherein a pyrazole derivative having the formula

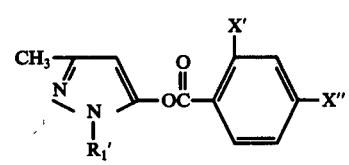

(II)' wherein
$R_1'$, X' and X'' have the same meanings as defined above is treated with a catalyst, the improvement which comprises said catalyst being an alkali metal carbonate in an amount of more than 1 equivalent more per mole of the pyrazole derivative (II)'.

5. A process as claimed in claim 4 in which sodium or potassium carbonate is used in an amount of 1.5-3.0 equivalent moles of the pyrazole derivative (II)'.

* * * * *